US009215976B2

(12) United States Patent
Itoh

(10) Patent No.: US 9,215,976 B2
(45) Date of Patent: Dec. 22, 2015

(54) OPHTHALMOLOGIC APPARATUS, PROGRAM, AND STORAGE MEDIUM OF PROGRAM

(75) Inventor: Hiroshi Itoh, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 495 days.

(21) Appl. No.: 13/117,021

(22) Filed: May 26, 2011

(65) Prior Publication Data

US 2011/0292339 A1    Dec. 1, 2011

(30) Foreign Application Priority Data

May 28, 2010    (JP) ................... 2010-123284

(51) Int. Cl.
*A61B 3/14* (2006.01)
*A61B 3/00* (2006.01)
(52) U.S. Cl.
CPC ........................................ *A61B 3/14* (2013.01)
(58) Field of Classification Search
USPC ......... 351/200, 205–207, 221–222, 203, 209, 351/214, 223, 243, 245, 246
See application file for complete search history.

(56) References Cited

U.S. PATENT DOCUMENTS

| 5,619,739 A * | 4/1997 | Kawabata ..................... 396/382 |
| 2009/0180072 A1 * | 7/2009 | Suzuki ......................... 351/207 |
| 2009/0244483 A1 * | 10/2009 | Yoshino et al. ............... 351/206 |

FOREIGN PATENT DOCUMENTS

| JP | 05-095904 A | 4/1993 |
| JP | 2007-37897 A | 2/2007 |

\* cited by examiner

*Primary Examiner* — Stephone B Allen
*Assistant Examiner* — Brandi Thomas
(74) *Attorney, Agent, or Firm* — Canon U.S.A., Inc. IP Division

(57) ABSTRACT

A control unit, if insertion of a diopter correction lens or retraction of the diopter correction lens is detected, moves a focusing lens to a position according to an insertion or retraction state of the diopter correction lens corresponding to a position of the focusing lens detected by a focusing lens position detection unit.

8 Claims, 6 Drawing Sheets

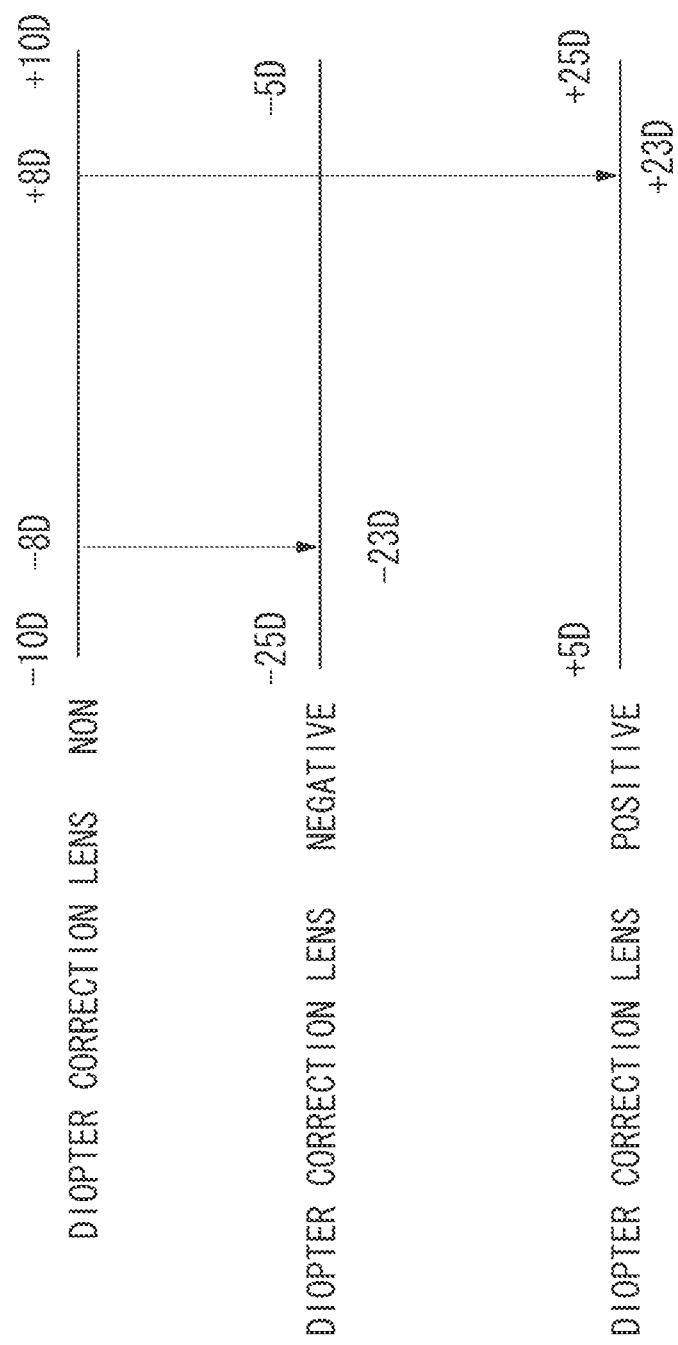

OPHTHALMOLOGIC APPARATUS, PROGRAM, AND STORAGE MEDIUM OF PROGRAM

BACKGROUND OF THE INVENTION

1. Field of the Invention

The present invention relates to a technique for performing diopter correction by inserting or retracting a diopter correction lens.

2. Description of the Related Art

A fundus camera that observes and photographs a fundus of an examinee's eye needs to respond to a very wide range of diopters of the order of 40 to 60 diopter that corresponds from a severe myopia to a severe hyperopia of the examinee's eye. However, it is difficult for a focusing lens of the fundus camera to respond to a range as wide as 40 to 60 diopter only by a movement of the focusing lens, in terms of the physical space of an optical arrangement.

Thus, an auxiliary lens having a positive or negative power referred to as a diopter correction lens is inserted into an observation photographing optical system. Accordingly, if an amount of a mechanistic movement of the focusing lens is narrow, the diopter correction lens enables the fundus camera to cover each of a region of the severe myopia, a region of the severe hyperopia and a region therebetween (i.e., a region where the diopter correction lens is not inserted), so that the fundus camera can respond to the wider diopters of the examinee's eye. In a general fundus camera, when the fundus of the examinee's eye cannot be brought into focus while the diopter correction lens is absent, an examiner inserts the diopter correction lens as appropriate to perform focusing.

On the other hand, in a technique discussed in Japanese Patent Application Laid-Open No. 2007-37897, two configurations for eliminating the need for an examiner to insert and retract a diopter correction lens are discussed. In the first configuration, diopter data of an examinee is input into the fundus camera in advance, and the fundus camera determines whether the diopter correction lens is needed or not based on the diopter data. If it is determined that the diopter correction lens is needed, the diopter correction lens is inserted without the need for the examiner to operate. In the second configuration, when the focusing lens comes to a predetermined position, the fundus camera determines that the diopter correction lens is needed, and then the diopter correction lens is inserted.

Although the diopter correction lens is very useful because it can enlarge a diopter correction range in which focusing can be performed with a simple configuration, there is an issue as follows. More specifically, when the diopter correction lens is inserted from a state where the diopter correction lens is absent, the diopter of the observation photographing optical system of the fundus camera will be greatly changed, and operability thereof will be impaired by the fact that continuity is lost in the diopter correction of the fundus camera.

This issue will be described below with reference to FIG. 6. An upper part in FIG. 6 indicates a diopter correction range of the fundus camera, when the diopter correction lens is absent. It indicates that a diopter correctable range is −10D to +10D. A middle part indicates the diopter range when a diopter correction lens having a negative power is inserted. In this case, the diopter correctable range is changed to −25D to −5D by inserting the diopter correction lens having the negative power. A lower part indicates the diopter range when a diopter correction lens having a positive power is inserted. In this case, the diopter correctable range is changed to +5D to +25D by inserting the diopter correction lens having the positive power.

For example, when an examiner photographs an examinee with the severe myopia (−15D), the examiner tries to move the focusing lens to −D side to bring into focus because the examiner has no idea of a diopter of the examinee. However, if the examiner determines that it cannot get focus at a position of 8D, for example, the examiner inserts a negative diopter correction lens. Thus, as illustrated in FIG. 6, a diopter of the fundus camera is changed from −8D to −23D, and continuity of the diopter correction is lost. For this reason, the examiner would wonder which direction to move the focusing lens. The same thing can be happen in a case of eyes with severe hyperopia which need the positive diopter correction lens. For example, upon determining that it cannot be brought into a focus at a position of +8D, the examiner inserts the positive diopter correction lens. Then, as illustrated in FIG. 6, the diopter of the fundus camera is changed from +8D to +23D, and thus continuity of the diopter correction is lost.

SUMMARY OF THE INVENTION

The present invention is directed to a technique capable of maintaining continuity of diopter correction, when a diopter correction lens is inserted or retracted.

According to an aspect of the present invention, an ophthalmologic apparatus includes an imaging optical system configured to image reflected light from a fundus by an imaging unit via a focusing lens, a correction unit configured to correct a diopter by inserting a diopter correction lens into the imaging optical system, and a control unit configured, if the diopter correction lens is inserted by the correction unit, to move a position of the focusing lens in a direction in which change in the diopter generated by insertion of the diopter correction lens is reduced.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 6 illustrates a state in which a diopter of an observation photographing optical system of the fundus camera is changed by inserting a diopter correction lens.

DESCRIPTION OF THE EMBODIMENTS

Various exemplary embodiments, features, and aspects of the invention will be described in detail below with reference to the drawings.

Figure 1:
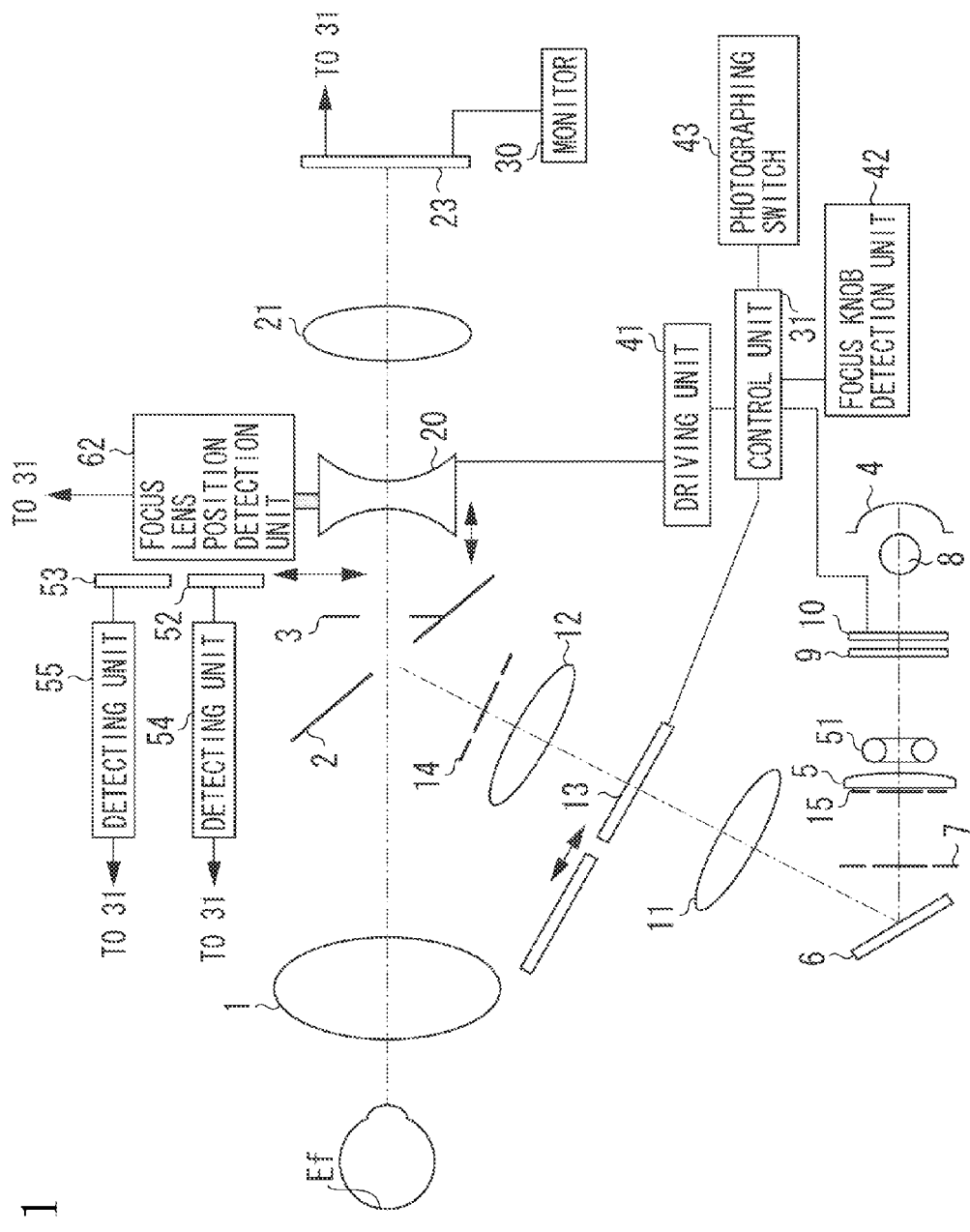
FIG. 1 illustrates a configuration of a fundus camera according to a first exemplary embodiment of the present invention.

A first exemplary embodiment of the present invention will be described. FIG. 1 illustrates a configuration of a fundus camera according to the first exemplary embodiment of the present invention. As illustrated in FIG. 1, in the fundus camera according to the present exemplary embodiment, a cornea stop 14 and relay lenses 11 and 12 are arranged on an optical path from an objective lens 1 via a perforated mirror 2, a xenon tube 51 serving as a photographing light source such as a strobe light source emitting a flashlight of a visible light, a halogen lamp 8 serving as an observation light source, and to a reflection mirror 4. The cornea stop 14 has a ring-shaped opening for separating an illumination light flux and a photographing light flux so that a harmful light (reflected light) from a cornea of an examinee's eye by the illumination light flux may not enter into a photographing stop 3.

A near-infrared cut filter 13 is arranged between the relay lenses 11 and 12. The near-infrared cut filter 13 is connected to a control unit 31. The control unit 31 performs control to cause the near-infrared cut filter 13 to be retracted to the outside the optical path during fundus observation, and to cause the near-infrared cut filter 13 to be inserted into the optical path during photographing. The above-described fundus camera has a configuration as an application example of a focusing lens control device according to the present invention.

A mirror 6 is arranged at the rear of the relay lens 11. Between the mirror 6 and the halogen lamp 8, there are arranged a crystalline lens stop 7 and a pupil stop 15. The crystalline lens stop 7 has a ring-shaped opening for separating the illumination light flux from the photographing light flux so that a harmful light (reflected light) from a crystalline lens of the examinee's eye by the illumination light flux may not enter into a photographing stop 3. The pupil stop 15 has a ring-shaped opening arranged at a position substantially conjugate with a position of a pupil of the examinee's eye. At the rear of the pupil stop 15, a lens 5 for enhancing effective use of a light emitted from the xenon tube 51, a diffusion plate 9, and a visible-light cut filter 10 which does not transmit a visible-light wavelength.

The illumination optical system is thus constituted by the optical system including components from the objective lens 1 via the perforated mirror 2 to the halogen lamp 8 serving as the observation light source including the reflection mirror 4. At the rear of the perforated mirror 2, there are arranged the photographing stop 3, a focusing lens 20, an imaging lens 21, and an imaging unit 23.

The focusing lens 20 is connected to a driving unit 41, and the driving unit 41 is connected to the control unit 31. The driving unit 41 drives the focusing lens 20 based on an output signal from the control unit 31. Further, the focusing lens 20 is provided with a focusing lens position detection unit 62 for detecting a position of the focusing lens 20, and an output signal therefrom is output to the control unit 31 at predetermined time intervals. The focusing lens position detection unit 62 is a configuration as an application example of a first detection unit according to the present invention.

Between the photographing stop 3 and the focusing lens 20, a negative diopter correction lens 52 and a positive diopter correction lens 53 are arranged to be insertable and retractable. Detection units 54 and 55 are connected to the negative diopter correction lens 52 and the positive diopter correction lens 53, respectively. The detection units 54 and 55 detect whether the respective diopter correction lenses are present in the optical path and output the detection results to the control unit 31. The detection units 54 and 55 are configuration as an application example of a second detection unit according to the present invention.

The imaging unit 23 has sensitivity from a visible light range to an invisible (near-infrared) light range, and can output moving image and still image data. However, the sensitivity in a near-infrared wavelength range is lower than that in a visible wavelength range. Therefore, when observation is performed in the near-infrared range, it is necessary to increase gains or to perform processing such as pixel addition by reducing resolution compared with the photographing in order not to put burden on the examinee. Such control is performed by the control unit 31. The components including from the objective lens 1 to the imaging unit 23 constitute the observation photographing optical system.

A focus knob detection unit 42 for detecting, when the examiner turns a focus knob (not illustrated) for focusing, an amount of the turning, and a photographing switch 43 for performing still image photographing are connected to the control unit 31. A table as illustrated in Table 1 is stored in the control unit 31.

Table 1 indicates that the focusing lens position is linearly changed at an interval of 2D using 0D as a reference position of the focusing lens, for the sake of simplicity. From the table, it can be understood that, for example, when the focusing lens is present at a position of −2 mm from the reference position, a diopter of the fundus camera is −4D if the diopter correction lens is absent in the optical path, and −19D, or +11D if the negative or the positive diopter correction lens is present within the optical path, respectively. In the present exemplary embodiment, a mechanistic movement width of the focusing lens 20 is 10 mm, i.e., −5 mm to +5 mm, as illustrated in Table 1.

TABLE 1

| | Focusing lens position (mm) | | | | | | | | | | |
|---|---|---|---|---|---|---|---|---|---|---|---|
| | −5 | −4 | −3 | −2 | −1 | 0 | +1 | +2 | +3 | +4 | +5 |
| Diopter (D) when diopter correction lens is absent | −10 | −8 | −6 | −4 | −2 | 0 | +2 | +4 | +6 | +8 | +10 |
| Diopter (D) when negative diopter correction lens is present | −25 | −23 | −21 | −19 | −17 | −15 | −13 | −11 | −9 | −7 | −5 |

TABLE 1-continued

| | Focusing lens position (mm) | | | | | | | | | | |
|---|---|---|---|---|---|---|---|---|---|---|---|
| | −5 | −4 | −3 | −2 | −1 | 0 | +1 | +2 | +3 | +4 | +5 |
| Diopter (D) when positive diopter correction lens is present | +5 | +7 | +9 | +11 | +13 | +15 | +17 | +19 | +21 | +23 | +25 |

The control unit 31 stores the position of the focusing lens 20, and when the focus knob detection unit 42 detects a turning direction and a turning amount of the focus knob, the control unit 31 outputs a signal for driving the focusing lens 20 to the driving unit 41 according to the turning amount. The imaging unit 23 is also connected to a monitor 30, and an image signal which has been output in a moving image or a still image is displayed on the monitor 30. The image signal to be displayed becomes an image signal in which an electronically created aperture mask is added to the image signal captured by the imaging unit 23.

Now, it is assumed that an examinee with a diopter of −15D is photographed. An examiner performs alignment between the examinee's eye and the fundus camera. Then, the examiner turns the focus knob to a direction to focus on the fundus. When the turning direction and the turning amount are detected by the focus knob detection unit 42, the control unit 31 moves the focusing lens 20 via the driving unit 41 according to the selected result.

Since the diopter of the examinee is −15D, a lens position moves to a minus (−) side. For example, when the focusing lens 20 is present at a position of −8D (position of −4 mm), the examiner determines that the fundus cannot be brought into focus without the diopter correction lens, and may insert the negative diopter correction lens 52. Then, the detection unit 54 outputs that the negative diopter correction lens 52 is inserted, to the control unit 31.

The control unit 31 recognizes that the focusing lens 20 is present at the position of −8D based on the output signal of the focusing lens position detection unit 62. Therefore, the control unit 31 calculates a position at which the diopter of the fundus camera becomes −8D and outputs a movement signal to the driving unit 41 so as to move the focusing lens 20 by a distance of 7.5 mm from the position of −4 mm to the position of +3.5 mm. Accordingly, the continuity of the diopter by the diopter correction lens can be maintained.

Since a focusing state is the same as a state before the diopter correction lens is inserted, the examiner can turns the focus knob in −D direction without hesitating about a moving direction of the focus knob, and moves the focusing lens 20 to −15D (position of 0 mm in the focusing lens position). When alignment and focusing are completed, the examiner presses a photographing switch 43.

Then, the control unit 31 inserts the near-infrared cut filter 13 in the illumination optical system into the optical path, and performs fundus photographing by causing the xenon tube 51 to emit a light after setting the imaging unit 23 to still image photographing.

If the examiner inserts the negative diopter correction lens 52 at a position of −4D, no position corresponding to −4D could exist in the diopter range when the negative diopter correction lens 52 is inserted. In this case, the control unit 31 causes the focusing lens 20 to move to a position of −5D (+5 mm) closest to an emmetropia in the diopter correction range (moveable range of the focusing lens 20) by the driving unit 41.

Conversely, it is assumed that the examiner removes the negative diopter correction lens 52 to the outside of the optical path from the state in which the focusing lens 20 is at a position of −7D (+4 mm in the focusing lens position) and the negative diopter correction lens 52 is inserted. Then, the detection unit 54 notifies the control unit 31 of that the negative diopter correction lens 52 is removed to the outside of the optical path.

The control unit 31 calculates a corresponding position and outputs a signal to the driving unit 41 to move the focusing lens 20 to a position of −7D (−3.5 mm in the focusing lens position) without the diopter correction lens. Accordingly, continuity can be provided to the diopter correction of the fundus camera.

If the negative diopter correction lens 52 is removed beyond the diopter correction range without the diopter correction lens, the continuity of the diopter cannot be provided. However, the focus lens is moved to a position closest to emmetropia so as to save the examiner from being confused with the direction to move the focus knob. More specifically, if the diopter correction lens 52 is removed to the outside of the optical path when the focusing lens 20 is at −13D (+1 mm in the focusing lens position), the control unit 31 controls the driving unit 41 to move the focusing lens 20 to a position of −10D (−5 mm in the focusing lens position). The series of control is similarly performed in the case of the positive diopter correction lens 53.

Figure 2:
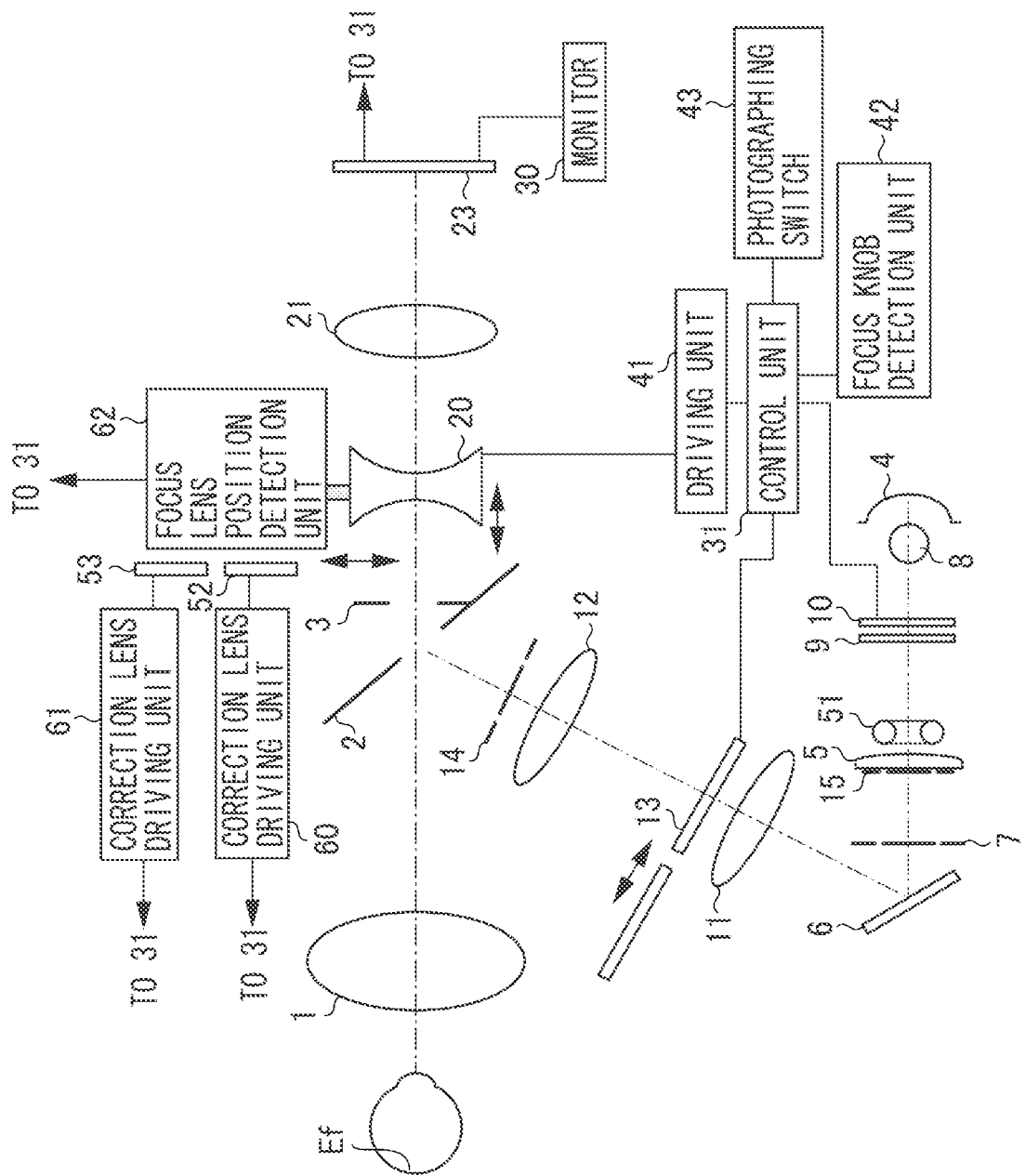
FIG. 2 illustrates a configuration of a fundus camera according to a second exemplary embodiment of the present invention.

Next, a second exemplary embodiment of the present invention will be described. FIG. 2 illustrates a configuration of the fundus camera according to the second exemplary embodiment of the present invention. For the similar configuration to that of the fundus camera according to the first exemplary embodiment, the same reference numerals in FIG. 1 are assigned to those in FIG. 2, and descriptions thereof will not be repeated.

In the observation photographing optical system, the negative diopter correction lens 52 is connected to a correction lens driving unit 60. The positive diopter correction lens 53 is connected to a correction lens driving unit 61. These two correction lens driving units 60 and 61 are connected to the control unit 31 and insert into and retract from the optical path the negative diopter correction lens 52 and the positive diopter correction lens 53 respectively under control of the control unit 31.

The control unit 31 includes a table as shown in Table 2 for determining whether to insert into or retract from the optical path the negative diopter correction lens 52 and the positive diopter correction lens 53 using the correction lens driving units 60 and 61 based on an output signal from the focusing lens position detection unit 62.

As illustrated in Table 2, numerical values of −5 mm and +5 mm of the focusing lens positions are stored in the table as first setting values for determining whether to insert the negative diopter correction lens 52 and the positive diopter correction lens 53 into the optical path. Further, in Table 2, numerical values of −4 mm and +4 mm of the focusing lens positions are stored as second setting values for determining whether to retract the negative diopter correction lens 52 and the positive diopter correction lens 53 to the outside of the optical path. A relationship between the position of the focusing lens and diopter when the negative diopter correction lens 52 or the positive diopter correction lens 53 is inserted into the optical path is the same as the relationship illustrated in Table 1 which is described in the first exemplary embodiment.

TABLE 2

| | Focusing lens position (mm) | | | | | | | | | |
|---|---|---|---|---|---|---|---|---|---|---|
| | −5 | −4 | −3 | −2 | −1 | 0 | +1 | +2 | +3 | +4 | +5 |
| Diopter (D) when diopter correction lens is absent | −10 | −8 | −6 | −4 | −2 | 0 | +2 | +4 | +6 | +8 | +10 |
| Position when negative diopter correction lens is inserted | Insert | | | | | | | | | | |
| Position when negative diopter correction lens is retracted | | retract | | | | | | | | | |
| Position when positive diopter correction lens is inserted | | | | | | | | | | | Insert |
| Position when positive diopter correction lens is retracted | | | | | | | | | | retract | |

Now, it is assumed that an examinee with a diopter of −15D is photographed. The examiner performs alignment between the examinee's eye and the fundus camera. Then, the examiner turns the focus knob to a direction to focus on the fundus. When the turning direction and the turning amount are detected by the focus knob detection unit 42, the control unit 31 moves the focusing lens 20 via the driving unit 41 according to the selected result. Since the diopter of the examinee is −15D, the lens position moves to a minus (−) D side.

When the focusing lens position detection unit 62 detects that the focusing lens 20 has come to a position of −5 mm, the control unit 31 causes the driving unit 60 to insert the negative diopter correction lens 52 into the optical path, since the position of the focusing lens 20 has reached the first setting value.

Further, the control unit 31 outputs a movement signal to the driving unit 41 to move the focusing lens 20 by a distance of 7.5 mm from the position of −5 mm to a position of +2.5 mm so that a diopter of the fundus camera becomes −10D. Accordingly, the continuity of the diopter by the diopter correction lens can be maintained.

Since the focusing state is the same as the state before the diopter correction lens is inserted, the examiner can turns the focus knob in the −D direction without hesitating about a moving direction of the focus knob, and moves the focusing lens 20 to −15D (position of 0 mm in the focusing lens position). When alignment and focusing are completed, the examiner presses a photographing switch 43. Then, the control unit 31 inserts the near-infrared cut filter 13 in the illumination optical system into the optical path, and performs fundus photographing by causing the xenon tube 51 to emit a light after setting the imaging unit 23 to the still image photographing.

Conversely, the examiner moves the focus knob in the +D direction, while the negative diopter correction lens 52 is inserted. If it is detected that the focusing lens 20 has come to a position of −8D (+3.5 mm in the focusing lens position), the control unit 3 determines that the focusing lens 20 has reached the second setting value and drives the correction lens driving unit 60 to retract the negative diopter correction lens 52 from the optical path. The control unit 31 outputs a signal to the driving unit 41 to move the focusing lens 20 to a position of −8D (−4 mm in the focusing lens position) without the diopter correction lens. Accordingly, continuity can be provided to the diopter correction of the fundus camera.

As illustrated in Table 2, in the case of the positive diopter correction lens 53, the series of control is performed such that the positive diopter correction lens 53 is inserted at +10D as the first setting value and is retracted at +8D as the second setting value.

Figure 3:
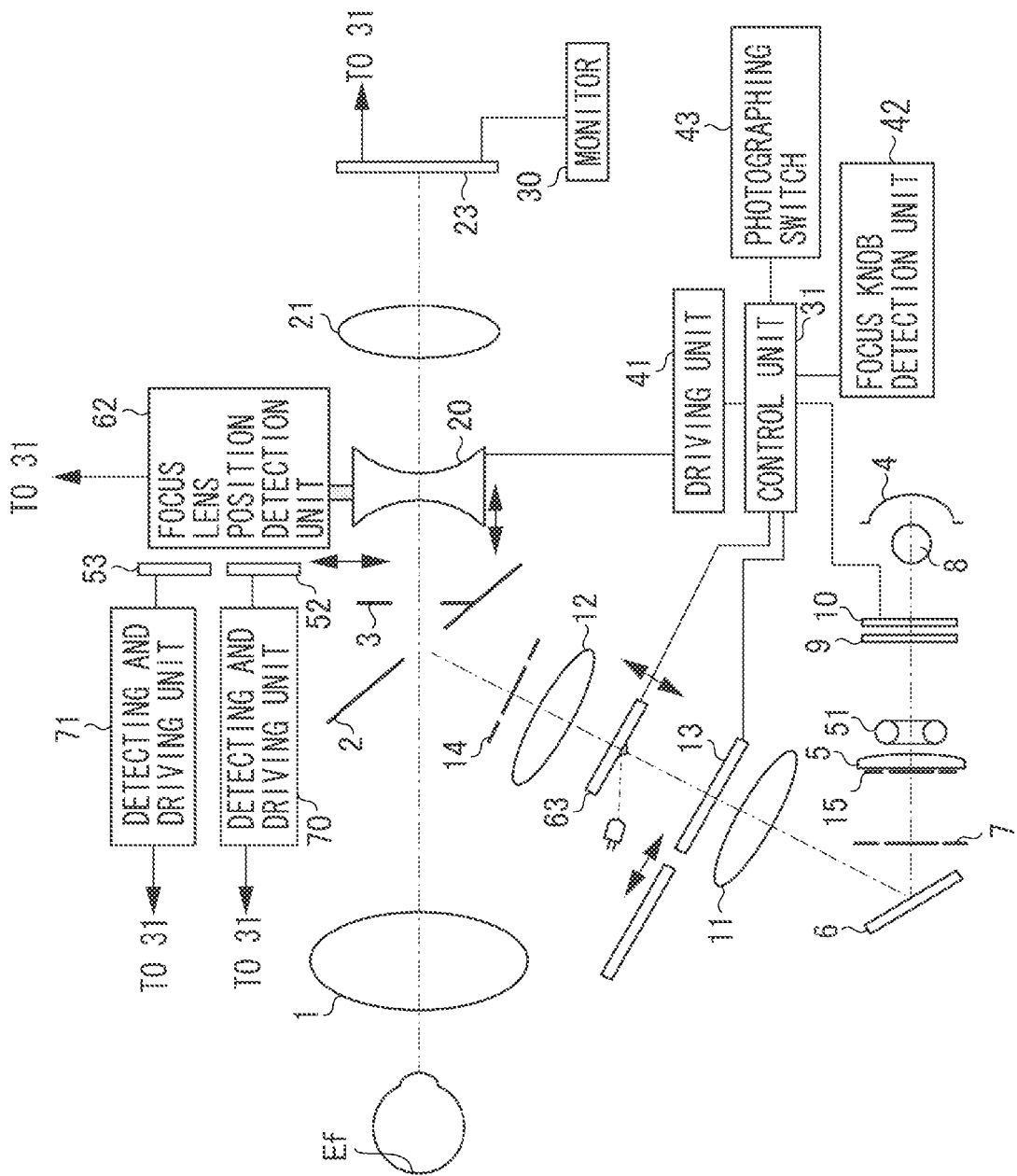
FIG. 3 illustrates a configuration of a fundus camera according to a third exemplary embodiment of the present invention.

Next, a third exemplary embodiment of the present invention will be described. FIG. 3 illustrates a configuration of the fundus camera according to the third exemplary embodiment of the present invention. In the following description, the same reference numerals as those in FIG. 1 and FIG. 2 are assigned to the components in the fundus camera similar to those described in the first and second exemplary embodiments are, and thus descriptions thereof will not be repeated.

In the second exemplary embodiment, determination of insertion and retraction of the diopter correction lens uses a table as shown in Table 2. In contrast, in the present exemplary embodiment, insertion and retraction of the diopter correction lens are determined from a position of the focusing lens 20, presence or absence of the negative diopter correction lens 52 and the positive diopter correction lens 53 in the optical path, and a split target image. Detecting and driving units 70 and 71 perform both detection of positions and driving of the negative diopter correction lens 52 and the positive diopter correction lens 53 respectively.

Figure 4:
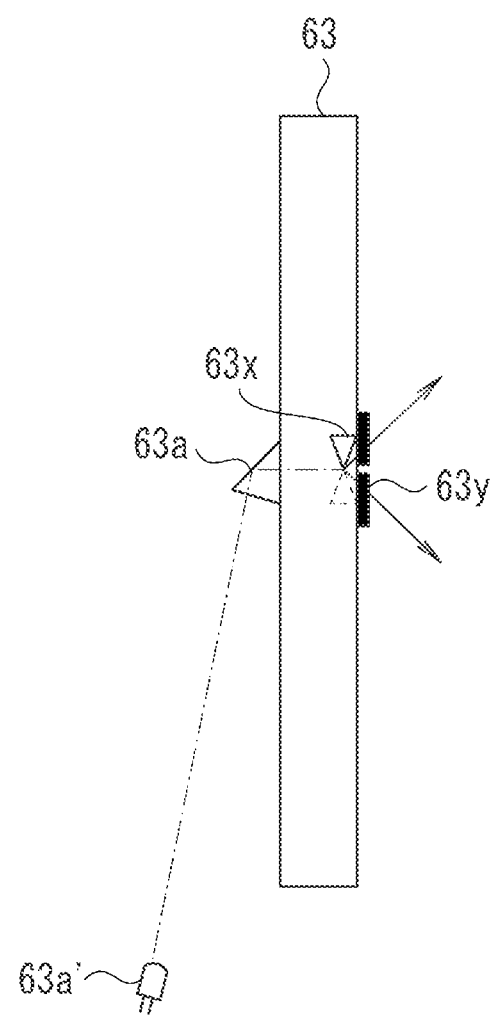
FIG. 4 illustrates a cross-sectional configuration of a split target member.

In the illumination optical system, a split target member 63 is arranged as a split target projection system for focusing on a position conjugate with the examinee's eye fundus. The split target member 63 moves in the optical axis direction interlocking with the focusing lens 20. FIG. 4 illustrates a cross-sectional configuration of the split target member 63. The split target member 63 is made of transparent material which transmits a light, such as acryl.

As illustrated in FIG. 4, a minute prism 63a is arranged on a surface of the split target member 63. The minute prism 63a is arranged roughly in the center of the split target member 63. The minute prism 63a is arranged to reflect a light flux emitted from a near-infrared light source 63a' for split which is arranged in the proximity of the split target member 63 in an optical axis direction of the illumination optical system. The split target member 63 includes a polarizing prism 63x and a rectangular opening 63y on a surface at opposite side of the minute prism 63a, and the above-described reflected light is separated here into two directions and becomes split targets for focusing.

Figure 5A:
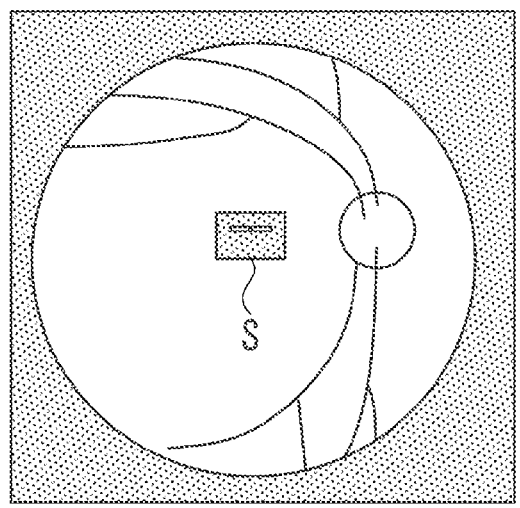
FIGS. 5A to 5C illustrate fundus images and split target images.
Figure 5B:
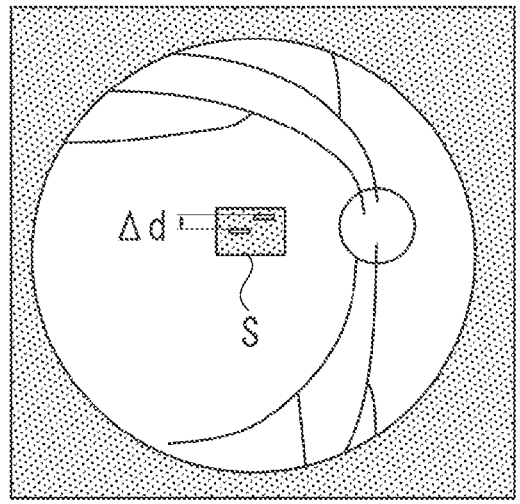
Figure 5C:
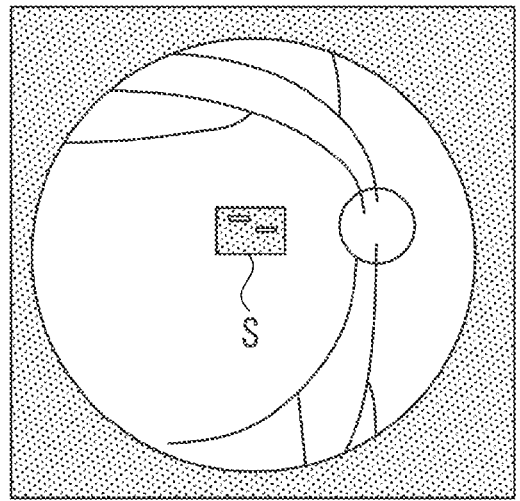

An observation screen of the fundus at this time can be observed as a moving image of the image data, which is formed such that an aperture mask is electronically added to a split target S and a fundus image on the monitor 30. FIG. 5A indicates an in-focus state, i.e., two bright lines of the split target S are in line with each other. FIGS. 5B and 5C indicate states in which the focuses are shifted to −D side and +D side, respectively. Since the directions to which the two bright lines are shifted depend on the deviation of diopter, the examiner can easily discriminate which way to move the focus knob when performing focusing.

Observation image information is output to the control unit 31. The control unit 31 performs image processing by segmenting a portion corresponding to the split target S illustrated in FIG. 5, and detects a deviation amount Δd of the bright lines, and a positional relationship of right and left bright lines. The present processing is an example of processing performed by a third detection unit according to the present invention.

Determination of whether the negative diopter correction lens 52 and the positive diopter correction lens 53 are inserted into and retracted from the optical path is performed by the control unit 31 according to three pieces of information as follows. The first information indicates a position of the focusing lens determined from a detected signal of the focusing lens position detection unit 62. The second information indicates whether the diopter correction lens 52 or 53 is present within the optical path. The third information indicates the deviation amount Δd and the positional relationship of the two bright lines of the split target.

The control unit 31 determines a current diopter of the fundus camera from the first and second information using the table as shown in Table 1. Further, the control unit 31 obtains information whether a diopter of the examinee's eye is at −D side or at +D side using the current diopter as the reference from the positional relationship of the bright lines based on the third information. Then, the control unit 31 obtains a difference between the current diopter (D) of the fundus camera and the diopter of the examinee's eye from the deviation amount Δd. Accordingly, the control unit 31 can determine the diopter of the examinee's eye.

The control unit 31 compares the diopter of the examinee's eye with the diopter correction range, and if the diopter of the examinee's eye exceeds the diopter correction range, performs determination to insert and retract the negative diopter correction lens 52 or the positive diopter correction lens 53. Then, the control unit 31 inserts or retracts the negative diopter correction lens 52 or the positive diopter correction lens 53 which becomes necessary, via the detecting and driving unit 70 or 71. A method for driving the focusing lens 20 to maintain the continuity of the diopter correction at the time of insertion and retraction is similar to the first and the second exemplary embodiments.

Now, it is assumed that an examinee with a diopter of −15D is photographed. The examiner performs alignment between the examinee's eye and the fundus camera. Then, the examiner turns the focus knob to a direction to focus on the fundus. It is assumed that the negative diopter correction lens 52 and the positive diopter correction lens 53 are not present in the optical path. When the turning direction and the turning amount of the focus knob are detected by the focus knob detection unit 42, the control unit 31 moves the focusing lens 20 via the driving unit 41 according to the detected result. A position of the moved focusing lens 20 is assumed to be −9D.

At the same time, if it is assumed that an image captured by the imaging unit 23 is the one in FIG. 5B, the control unit 31 segments the region S, and performs image processing. As the result, since the right bright line is above the left bright line from the positional relationship between right and left split bright lines, it can be understood that the examinee's eye diopter is in the −D side than −9D.

Further, since a deviation amount Δd of split indicates deviation of three splits based on a height of the split bright line (assumed that one split corresponds to deviation of 2D), it can be understood that the examinee's eye diopter is deviated by 6D from −9D. Accordingly, the control unit 31 calculates the diopter of the examinee's eye as −9D−6D=−15D, and determines that the diopter exceeds the diopter correction range −10D of the fundus camera without the negative diopter correction lens 52 and the positive diopter correction lens 53. Thus, the control unit 31 inserts the negative diopter correction lens 52 into the optical path via the driving unit 60.

The present invention can also be realized by executing the following processing. More specifically, software (a program) for realizing the functions of the above exemplary embodiments is supplied to a system or an apparatus via a network or various storage media and a computer (or CPU or micro processing unit (MPU)) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-123284 filed May 28, 2010, which is hereby incorporated by reference herein in its entirety.

What is claimed is:

1. An ophthalmologic apparatus comprising:
    an imaging optical system configured to image reflected light from a fundus by an imaging unit via a focusing lens;
    a correction unit configured to correct a diopter by inserting a diopter correction lens into an optical path of the imaging optical system; and
    a control unit configured to control the correction unit,
    wherein the control unit is configured, if movement of the focusing lens to a position within a movable range of the focusing lens is detected while the diopter correction lens is not in the optical path, to control the correction unit to insert the diopter correction lens into the optical path and move a position of the focusing lens in a direction in which change in the diopter generated by insertion of the diopter correction lens is reduced, and
    wherein the control unit is configured, if movement of the focusing lens to a position within a movable range of the focusing lens and away from an end of the movable range by a predetermined distance is detected while the diopter correction lens is in the optical path, to control the correction unit to retract the diopter correction lens from the optical path and move a position of the focusing lens in a direction in which change in the diopter generated by retraction of the diopter correction lens is reduced.

2. The ophthalmologic apparatus according to claim 1, further comprising:

a first detection unit configured to detect a position of the focusing lens which causes the reflected light from the fundus to form an image on the imaging unit, wherein if the diopter correction lens is inserted by the correction unit, the control unit moves the position of the focusing lens based on position information about the focusing lens detected by the first detection unit.

3. The ophthalmologic apparatus according to claim 1, further comprising:

a second detection unit configured to detect an insertion of a positive or negative diopter correction lens into the optical path for causing the reflected light from the fundus to form an image on the imaging unit and a retraction of the diopter correction lens from the optical path, wherein if insertion of the diopter correction lens or retraction of the diopter correction lens is detected by the second detection unit, the control unit moves the focusing lens to a position according to an insertion or retraction state of the diopter correction lens.

4. The ophthalmologic apparatus according to claim 1, wherein if a position to which the focusing lens to be moved is not included in a movable range of the focusing lens, the control unit moves the focusing lens to a position closest to the position to which the focusing lens to be moved in the movable range.

5. The ophthalmologic apparatus according to claim 1, wherein if it is detected that the focusing lens has moved to a predetermined position, the control unit controls insertion of the diopter correction lens into the optical path for causing the reflected light from the fundus to form an image on the imaging unit.

6. The ophthalmologic apparatus according to claim 1, further comprising:

a third detection unit configured to detect a deviation amount of focus, wherein the control unit controls insertion of the diopter correction lens into the optical path or retraction of the diopter correction lens from the optical path according to a diopter of an examinee's eye determined based on a detection result of the third detection unit.

7. An ophthalmologic method comprising:

imaging reflected light from a fundus by an imaging unit of an imaging optical system via a focusing lens;

correcting a diopter by inserting a diopter correction lens into an optical path of the imaging optical system;

controlling, if movement of the focusing lens to a position within a movable range of the focusing lens is detected while the diopter correction lens is not in the optical path, inserting of the diopter correction lens into the optical path and moving of a position of the focusing lens in a direction in which change in the diopter generated by insertion of the diopter correction lens is reduced; and controlling, if movement of the focusing lens to a position within a movable range of the focusing lens and away from an end of the movable range by a predetermined distance is detected while the diopter correction lens is in the optical path, retracting the diopter correction lens from the optical path and moving a position of the focusing lens in a direction in which change in the diopter generated by retraction of the diopter correction lens is reduced.

8. A non-transitory storage medium that stores a program for causing a computer to execute an ophthalmologic method comprising:

imaging reflected light from a fundus by an imaging unit of an imaging optical system via a focusing lens;

correcting a diopter by inserting a diopter correction lens into an optical path of the imaging optical system;

controlling, if movement of the focusing lens to a position within a movable range of the focusing lens is detected while the diopter correction lens is not in the optical path, inserting of the diopter correction lens from the optical path and moving of a position of the focusing lens in a direction in which change in the diopter generated by insertion of the diopter correction lens is reduced; and controlling, if movement of the focusing lens to a position within a movable range of the focusing lens and away from an end of the movable range by a predetermined distance is detected while the diopter correction lens is in the optical path, retracting the diopter correction lens from the optical path and moving a position of the focusing lens in a direction in which change in the diopter generated by retraction of the diopter correction lens is reduced.

* * * * *